United States Patent [19]

Schneider et al.

[11] 4,341,909

[45] Jul. 27, 1982

[54] PREPARATION OF LOW MOLECULAR WEIGHT POLYHYDROXYL COMPOUNDS

[75] Inventors: Gottfried Schneider; Kuno Wagner; Hanns P. Müller, all of Leverkusen, Fed. Rep. of Germany

[73] Assignee: Bayer Aktiengesellschaft, Leverkusen, Fed. Rep. of Germany

[21] Appl. No.: 301,609

[22] Filed: Sep. 14, 1981

Related U.S. Application Data

[63] Continuation of Ser. No. 829,172, Aug. 30, 1977, abandoned.

[30] Foreign Application Priority Data

Aug. 31, 1976 [DE] Fed. Rep. of Germany ....... 2639084

[51] Int. Cl.$^3$ ..................... C07C 47/19; C08G 18/32; C08G 18/14
[52] U.S. Cl. .................................. 568/863; 521/158; 528/85
[58] Field of Search .................................... 568/863

[56] References Cited

U.S. PATENT DOCUMENTS

| | | | |
|---|---|---|---|
| 2,224,910 | 12/1940 | Hanford et al. ..................... | 568/863 |
| 2,760,983 | 8/1956 | MacLean et al. ................... | 260/594 |
| 2,775,621 | 12/1956 | MacLean et al. ................... | 568/863 |
| 2,879,307 | 3/1959 | Von Bezard et al. .............. | 568/863 |
| 3,838,006 | 9/1974 | Hijiya et al. ........................ | 568/863 |

FOREIGN PATENT DOCUMENTS

| | | | |
|---|---|---|---|
| 740245 | 10/1943 | Fed. Rep. of Germany ...... | 568/863 |
| 851493 | 10/1952 | Fed. Rep. of Germany ...... | 568/863 |
| 881504 | 6/1953 | Fed. Rep. of Germany . | |
| 311788 | 5/1929 | United Kingdom ................ | 568/863 |
| 513708 | 10/1939 | United Kingdom . | |
| 745557 | 2/1956 | United Kingdom ................ | 568/863 |

OTHER PUBLICATIONS

Gaylord, Polyethers, Part I, Interscience, N.Y. (1963), pp. 105-106, 197-200.
Schönfeldt, Surface-Active Ethylene Oxide Adducts, Pergamon, Oxford (1969), pp. 297, 534-535, 565.
Shigemasa et al., Bull. Chem. Soc. Japan, vol. 50 (6), pp. 1527-1531, (1977).
Weiss et al., Jour. Catalysis, vol. 48, pp. 354-364, (1977).

*Primary Examiner*—H. S. Cockeram
*Attorney, Agent, or Firm*—Gene Harsh; Joseph C. Gil

[57] ABSTRACT

A process is disclosed for preparing mixtures of low molecular weight polyhydroxyl compounds and optionally hydroxyaldehydes and ketones by condensing formaldehyde hydrate with itself in the presence of (A) soluble or insoluble lead(II) salts or of divalent lead attached to a high molecular weight carrier; and (B) a co-catalyst, comprising a mixture of hydroxyaldehydes and hydroxyketones obtainable by condensation of formaldehyde, which mixture contains at least 75%, by weight, of $C_3$ to $C_6$ compounds and is characterized by the following molar ratios:

Compounds having 3 carbon atoms/compounds having 4 carbon atoms from 0.5:1 to 2.0:1;
Compounds having 4 carbon atoms/compounds having 5 carbon atoms from 0.2:1 to 2.0:1;
Compounds having 5 carbon atoms/compounds having 6 carbon atoms from 0.5:1 to 5.0:1.

The pH of the reaction mixture is held at from 6.0 to 7.0 until from 10 to 60% conversion has occurred and is then lowered to between 4.0 to 6.0 until 90–100% conversion has occurred. The reaction is then stopped by inactivating the catalyst.

9 Claims, No Drawings

PREPARATION OF LOW MOLECULAR WEIGHT POLYHYDROXYL COMPOUNDS

This application is a continuation, of application Ser. No. 829,172, filed Aug. 30, 1977 now abandoned.

BACKGROUND OF THE INVENTION

Polyhydroxyl compounds have attained great technical importance in numerous fields. For example, they are used on a large technical scale for the production of non-ionic surface active compounds, as anti-freezes, moisture-retainers and anti-hardeners and as starting components for the production of synthetic resins, such as polyester and polyether resins.

Polyhydric alcohols are at present obtained from natural products, such as sugar or cellulose materials, or synthesized by oxidation of petroleum derivatives.

In view of the world food situation, it appears unsuitable to use natural substances as raw materials for industrial products if they may be used as sources of dietary carbohydrates. On the other hand, due to the shortage of sources of petroleum, there has been a constant increase in the price of products which are dependent upon petroleum. Moreover, there are many uncertainties regarding the long term supply of petroleum products. It would therefore be desirable to find processes for the manufacture of polyhydroxyl compounds which do not depend for their supply of raw material on naturally occurring substances and petroleum.

Since the work by Butlerow and Loew (Ann. 120, 295 (1861) and J. pr. Chem. 33, 321 (1886)) in the previous century, it is known that condensation of formaldehyde hydrate (the term "condensation of formaldehyde" used in this text should be understood to mean in all cases "condensation of formaldehyde hydrate with itself") under the influence of basic compounds, such as calcium hydroxide or lead hydroxide, leads to the formation of hydroxyaldehydes and hydroxyketones. Since formaldehyde may be obtained from coal or natural gas by way of methanol, this would, in principle, be one way of obtaining hydroxyl compounds which would not depend on the supply of petroleum. Polyhydric alcohols could be synthesized by electrolytic reduction or catalytic or chemical hydrogenation.

In spite of numerous proposals for the synthesis of polyhydroxyl compounds by condensation of formaldehyde, however, no technically viable process has yet been developed for this synthesis because no one has yet succeeded in synthesizing mixtures of polyhydroxyl compounds in which the hydroxyl functionality is precisely reproducible. Moreover, the known processes result in the formation of hydroxyaldehyde and hydroxyketone mixtures which may only be hydrogenated with difficulty and only with the use of very large quantities of catalysts. This high catalyst consumption has hitherto made the synthesis of polyhydroxyl compounds by condensation of formaldehyde hydrate appear uneconomical. This has prevented condensation of formaldehyde hydrate from being used as the basis of a technical process for the synthesis of polyhydric alcohols.

Due to the disproportionation of formaldehyde into methanol and formic acid which takes place at the same time, only moderate yields have hitherto been obtained by the known processes so that working-up of the aqueous or aqueous alcoholic solutions obtained was very expensive.

It is well known that disproportionation of formaldehyde into methanol and formic acid is powerfully catalyzed by basic compounds. As was found by Pfeil, Chemische Berichte 84, 229 (1951), the reaction velocity of this so-called "Cannizzaro" reaction depends on the square of the formaldehyde concentration, while the reaction velocity of formaldehyde polyaddition (C—C linkage) depends on the formaldehyde concentration in a linear relationship (Pfeil and Schroth, Chemische Berichte 85, 303 (1952)). As the aldehyde concentration increases, therefore, the proportion of the desired polyhydroxyl compounds to methanol and formic acid obtained is shifted in favor of the unwanted compounds. It is for this reason that most of the known art processes propose to carry out the condensation of formaldehyde to hydroxyaldehydes and hydroxyketones in solutions which have a low formaldehyde concentration with a view to keeping the quantity of by-products as low as possible. However, the water used as solvent must then be removed by distillation in order to obtain the hydroxyaldehydes and hydroxyketones formed. This entails considerable energy costs due to the high heat of evaporation of water. Processes for the condensation of formaldehyde from dilute aqueous solutions are therefore uneconomical. Moreover, if distillation is prolonged, decomposition and discoloration reactions of the hydroxyaldehydes and hydroxyketones formed take place to a considerable extent.

It would therefore be desirable to carry out the condensation of formaldehyde from commercially obtainable concentrated formalin solutions without unwanted side reactions. In German Pat. No. 822,385 a process for the preparation of aliphatic hydroxy aldehydes is described in which a 40% formalin solution is reacted with thallium or thallium hydroxide. This process, however, is undesirable because of the toxicity of thallium and the fact that thallium hydroxide is difficult to obtain. Furthermore, the yields of this process are relatively low, being only from 70 to 80%.

Still with a view to preventing the Cannizzaro reaction, it has also been proposed to react formaldehyde solutions with calcium hydroxide or lead hydroxide in the presence of methanol, ethanol or other polar organic solvents (German Pat. No. 830,951 and Gorr and Wagner, Biochemische Zeitschrift, 262, 361 (1933)).

However, the addition of organic solvents again reduces the formaldehyde content of the solution. This process therefore also seems uneconomical on account of the additional energy costs required for evaporating off the added solvent to work-up the hydroxyaldehydes and ketones formed. Moreover, formaldehyde and lower alcohols give rise to unstable semiacetals which decompose under the conditions of the condensation reaction, with spontaneous liberation of the alcohols. Vigorous boiling phenomena therefore occur in the course of condensation reactions which are carried out at reaction temperatures above the boiling point of the given alcohol, particularly if large quantities of reaction mixture are used. These condensation processes cannot be carried out on a production-level without danger under such conditions.

A process for the preparation of oxy-oxo compounds has been described in German Pat. No. 884,794, in which aqueous formaldehyde solutions at concentrations of up to 30% are reacted with lead oxide or lead acetate and inorganic bases to form sugar-like compounds which reduce Fehling's solution in the cold. In this process, however, the formaldehyde solution must be heated for from 7 to 8 hours. The volume/time yield obtained therefore is not at all satisfactory. The relatively low yields (about 80%, based on the quantity of formaldehyde put into the process) are also by no means satisfactory.

A process for the preparation of hydroxyaldehydes and hydroxyketones has been disclosed in U.S. Pat. No. 2,224,910, in which exothermic condensation of formaldehyde is regulated by controlled addition of inorganic or organic bases to a formaldehyde solution containing compounds of lead, tin, calcium, barium, magnesium, cerium or thorium and a compound which is capable of enediol formation, such as glucose, ascorbic acid, fructose, benzoin, glycol aldehyde, erythrose, reductone, invert sugar or condensation products of formaldehyde. Although a mixture of hydroxyaldehydes and hydroxyketones is obtained from more highly concentrated formaldehyde solutions by this process without the addition of organic solvents, this is achieved only at the expense of various advantages. Thus, if the reaction is carried out at low pH values, the products obtained are mainly hydroxyaldehyde and hydroxyketone mixtures having a low hydroxyl functionality. Moreover, only moderate reaction velocities are achieved at low pH values so that the volume/time yields of this embodiment of the process are not satisfactory. To overcome these disadvantages, it is recommended in the above reference to start formaldehyde condensation at low pH values and then complete it at higher pH values. However, at pH values $\geq 7$, lead-catalyzed formaldehyde condensation is so rapid, spontaneous and uncontrolled that mixtures of hydroxyaldehydes and hydroxyketones cannot be obtained with reproducible distribution of the components because the reaction times and conditions may no longer be accurately controlled. Furthermore, it is known that hydroxyaldehydes, hydroxyketones and monosaccharides decompose into dark colored, partially carboxyl-containing compounds in an alkaline medium at elevated temperatures.

These decomposition reactions are most pronounced in the preferred embodiments of the process according to U.S. Pat. No. 2,224,910, particularly when the major proportion of formaldehyde has already undergone reaction. Hydroxyaldehyde and hydroxyketone mixtures of the type prepared by the process according to U.S. Pat. No. 2,224,910 therefore contain decomposition products which have acid groups and the mixtures are brown in color and cannot be obtained reproducibly. Moreover, hydrogenation of these mixtures succeeds only with uneconomically large quantities of Raney nickel caatalyst. Hydrogenation of a mixture of hydroxyaldehydes and hydroxyketones equivalent to 100 g of formaldehyde requires 30 g of Raney nickel.

The product mixtures obtained by the last-described method must, in all cases, by worked-up by distillation for purification and for recovery of hydroxyl compounds of low molecular weight. It would, however, be desirable to dispense with the distillation of the mixture, which requires additional costs in energy and apparatus, and to obtain the product mixtures in such a way that they are ready for use as soon as the water of solution has been removed, without being first distilled. Such colorless reaction mixtures, substantially free from by-products are not obtainable by processes known in the art.

It is therefore an object of the present invention to provide a process for the synthesis of mixtures of polyhydroxyl compounds which are as far as possible free from decomposition products and which may easily be hydrogenated to polyhydric alcohols using small quantities of hydrogenation catalysts. The mixtures of polyhydroxyl compounds obtained should be colorless and require no further purification.

It is a further object of the present invention to control the condensation of formaldehyde so that the distribution of products in the resulting mixtures of low molecular weight polyhydroxyl compounds could be reproducibly varied as required.

German Pat. No. 881,504 generally discloses the use of formose (a mixture of hydroxyaldehydes and hydroxyketones obtainable by the condensation of formaldehyde) as a co-catalyst for the condensation of formaldehyde under slightly acidic reaction conditions. The patent discloses the use of a number of metal catalysts including lead oxide and lead hydroxide, however, it does not teach or suggest the combination of features which is critical for the process of the present invention.

DESCRIPTION OF THE INVENTION

The surprising and completely unexpected finding has now been made that mixtures of hydroxyaldehydes, hydroxyketones and polyhydric alcohols which are free from reducing groups, in which mixtures the proportion of polyhydric alcohols (produced by crossed Cannizzaro reaction) is advantageously from 30 to 75%, by weight, may be obtained with excellent volume/time yields if condensation of formaldehyde hydrate is carried out in the presence of soluble or insoluble lead(II) salts used as catalyst, optionally bound to a high molecular weight carrier, and in the presence of a co-catalyst consisting of a mixture of hydroxyaldehydes and hydroxyketones such as is obtained from the condensation of formaldehyde hydrate, which mixture is characterized by the following molar ratios:

Compounds having 3 carbon atoms/compounds having 4 carbon atoms from 0.5:1 to 2.0:1;
Compounds having 4 carbon atoms/compounds having 5 carbon atoms from 0.2:1 to 2.0:1;
Compounds having 5 carbon atoms/compounds having 6 carbon atoms from 0.5:1 to 5.0:1;
the proportion of components having from 3 to 6 carbon atoms being at least 75%, by weight, preferably more than 85%, by weight, based on the total quantity of co-catalyst.

The reaction temperature employed is generally from 70° to 110° C., preferably from 80° to 100° C. and the pH of the reaction solution is adjusted by controlled addition of an inorganic or organic base so that it is maintained at from 6.0 to 7.0, preferably from 6.5 to 7.0, until the conversion reaches from 10 to 60%, preferably from 30 to 50%. Thereafter it is adjusted in the second phase of the reaction to a value of from 4.0 to 6.0, preferably from 5.0 to 6.0 so that the pH value is lower by 0.5 to 3.0 units, preferably 0.8 to 1.7 units, than in the first phase. It was surprisingly found that by controlling the pH in this particular manner and subsequently cooling the reaction mixture or stopping the reaction in another suitable manner at different residual formaldehyde contents (from 0 to 10%, by weight, preferably from 0.5 to 6%, by weight), the distribution of products in the mixtures of polyol, hydroxyaldehyde and hydroxyketone obtained could be varied in a reproducible manner.

The present invention thus relates to a process for the preparation of mixtures of low molecular weight polyhydroxyl compounds and optionally hydroxyaldehydes and hydroxyketones by condensation of formaldehyde in the presence of compounds of divalent lead as catalysts and in the presence of co-catalysts consisting of mixtures of hydroxyaldehydes and hydroxyketones. The process is carried out at a reaction temperature of from 70° to 110° C., preferably from 80° to 100° C. Aqueous formaldehyde solutions and/or paraformaldehyde dispersions containing from 20 to 65%, by weight, of formaldehyde are condensed in the presence of:
- (A) soluble or insoluble lead(II) salts or of divalent lead bound to a high molecular weight carrier; and
- (B) a co-catalyst consisting of a mixture of hydroxyaldehydes and hydroxyketones such as is obtained from the condensation of formaldehyde, which mixture contains at least 75%, by weight, of $C_3$–$C_6$ compounds and is characterized by the following molar ratios:

Compounds having 3 carbon atoms/compounds having 4 carbon atoms from 0.5:1 to 2.0:1;
Compounds having 4 carbon atoms/compounds having 5 carbon atoms from 0.2:1 to 2.0:1;
Compounds having 5 carbon atoms/compounds having 6 carbon atoms from 0.5:1 to 5.0:1.

The pH of the reaction solution is adjusted by controlled addition of an inorganic or organic base so that the pH is maintained at from 6.0 to 7.0 up to a conversion of from 10 to 60%, preferably from 30 to 50%, and is thereafter adjusted to from 4.0 to 6.0. Condensation of the formaldehyde hydrate is stopped by cooling and/or by inactivation of the lead catalyst by the addition of acids when the residual formaldehyde content in the reaction mixture is from 0 to 10%, preferably from 0.5 to 6.0%, by weight, of formaldehyde. The catalyst is subsequently removed in known manner and, if indicated, the aldehyde and keto groups present in the reaction product are reduced to hydroxyl groups.

For purposes of this invention, the catalyst and cocatalyst are generally introduced into an aqueous formaldehyde solution. This invention does not encompass the use of formaldehyde vapor which can be introduced into aqueous mixture of catalyst and co-catalyst.

Although it is known that hydroxyaldehydes and hydroxyketones may be reduced by formaldehyde (for example pentaerythritol may be synthesized from acetaldehyde and formaldehyde, acetaldehyde being first methylolated to pentaerythrose which is then reduced by excess formaldehyde), these crossed Cannizzaro reactions may only be carried out in a strongly alkaline medium. It was therefore extremely surprising to find that in the process according to the present invention, these reductions proceed with yields of from 30 to 75% even in acid pH ranges. It is advantageous that a large proportion of the carbonyl groups are reduced in this way so that subsequent removal of the remaining carbonyl groups by hydrogenation or reduction is considerably simplified.

Another surprising finding was that according to the present invention, highly concentrated aqueous solutions of polyols, hydroxyaldehydes and hydroxyketones which were completely colorless and therefore required no further purification or decolorization were obtained in yields of up to from 95 to 98% and with high reproducibility of the average OH functionality, whereas in the known art processes, as mentioned above, undesirable, strongly colored by-products which cannot be removed or can only be removed with great difficulty and additional expense, are formed as a result of decomposition reactions. Apart from this formation of by-products, the strongly colored solutions obtained according to the known art cannot be hydrogenated to polyhydric alcohols or at best can only be hydrogenated with difficulty and in low yields, whereas the colorless reaction mixtures obtained according to the present invention may easily be catalytically hydrogenated after the lead catalyst has been removed by simple precipitation reactions, this hydrogenation being achieved under mild reaction conditions of the type generally employed for the catalytic hydrogenation of sugars.

In the process according to the present invention, glycol aldehyde is first formed from two molecules of formaldehyde hydrate. Glyceraldehyde is then formed by further addition of formaldehyde hydrate in accordance with the following reaction scheme:

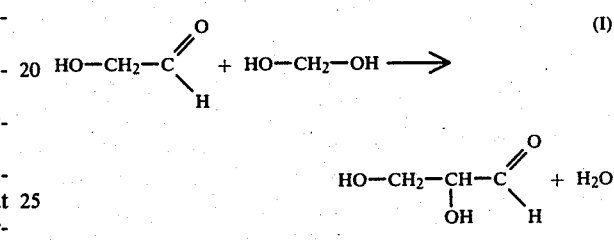

Numerous secondary reactions take place to give rise to the mixtures of hydroxyaldehydes and ketones obtainable according to the present invention. Only a few of these reactions are exemplified below:

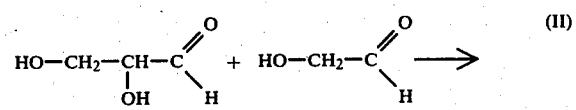

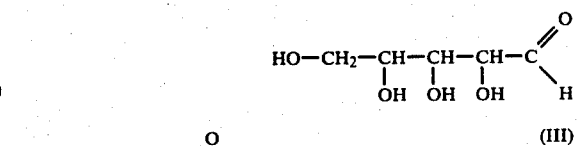

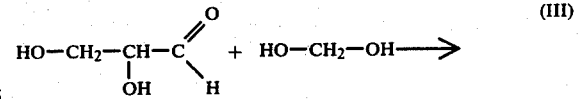

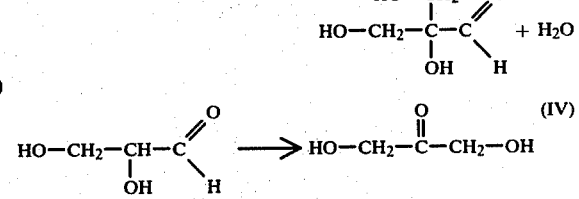

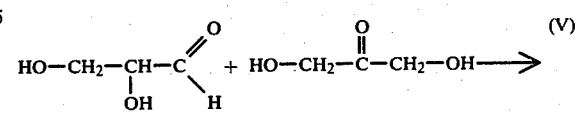

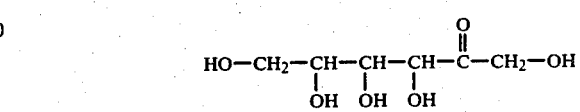

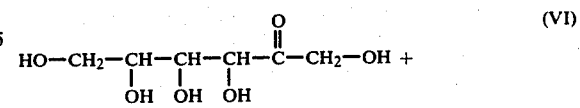

-continued

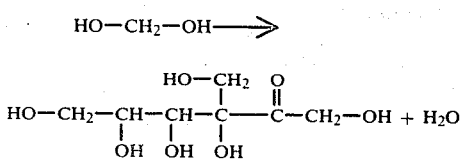

Gas chromatographic analysis of various product mixtures prepared according to the present invention shows that in the process according to the present invention it is possible not only to vary the distribution of products by stopping the reaction at different residual formaldehyde contents, but also to adjust the distribution of products completely reporducibly both in the range of compounds having from 2 to 4 carbon atoms and in the range of compounds having 5 or more carbon atoms. This was not be expected in view of the large number of reactions, of which only a few are indicated above, which may take place simultaneously in the process according to the present invention.

Condensation of formaldehyde in the process according to the present invention is preferably carried out in aqueous formaldehyde solutions of the conventional commercial concentrations (from 30 to 50%, by weight, of formaldehyde) which have been stabilized with methanol or other known stabilizers. On the other hand, unstabilized formaldehyde solutions containing a proportion of solid, polymerized formaldehyde and/or paraformaldehyde dispersions may also be used since these substances are dissolved by depolymerization in the course of the process according to the present invention and also condensed to hydroxyaldehydes and hydroxyketones. Condensation may also be carried out from even more highly concentrated formaldehyde solutions which may be obtained, for example, by depolymerization of paraformaldehyde or by concentration of dilute formaldehyde solutions in a vacuum. Thus, for example, hydroxyaldehydes and hydroxyketones may be obtained in very high yields by condensing a 65% formaldehyde solution which has been obtained by concentrating a 37% formaldehyde solution by evaporation under vacuum. The process according to the present invention is, of course, also applicable to less concentrated formaldehyde solutions, but such solutions are less suitable from an economic point of view on account of the additional energy costs required for evaporation of the solvent.

The formation of hydroxyaldehydes and hydroxyketones proceeds extremely rapidly in the process according to the present invention. For example, approximately 80% of the formaldehyde provided as starting material has generally been reacted after a reaction time of only 30 minutes. After 40 minutes the formaldehyde content of the solution is generally reduced to 1 to 1.5%, which corresponds to a conversion of from 96 to 97% of the formaldehyde. The volume/time yields of the process according to the present invention are thus superior to all known processes for the preparation of hydroxyaldehyde and hydroxyketones by condensation of formaldehyde. The volume/time yield is improved by a factor of from 12 to 14 in comparison with that obtained by the processes mentioned in German Pat. No. 884,794, for example.

Condensation of formaldehyde with formation of hydroxyaldehydes and hydroxyketones in accordance with the present invention is preferably promoted by water-soluble compounds of lead. These preferred catalysts (apart from the lead containing ion exchangers discussed below) include lead(II) acetate, lead(II) formate and lead(II) nitrate. The quantity of catalyst used according to the present invention is from about 0.01 to 10%, by weight, preferably from 0.1 to 5%, by weight, based on the formaldehyde put into the process.

In the process according to the present invention, the lead(II) ions are generally removed by precipitation with carbonate ions before the reaction products are worked-up or hydrogenated. It is particularly advantageous, and desirable on ecological grounds, that these precipitated lead salts may be reused as catalysts, either directly or by way of the acetate. Formation of the ecologically undesirable waste products occurring in the known processes is thus avoided in the process according to the present invention. In view of the fact that the lead catalyst is recirculated, the process according to the present invention is therefore superior to the known processes on ecological and economical grounds.

The divalent lead ions used as catalyst may also be removed as elemental lead by electrolytic deposition. Here again, the lead may be returned to the process as catalyst, for example, by converting it into the acetate.

Divalent lead ions may also be quite easily removed from the reaction solution by pumping the solution over cation-active ion exchangers. Reaction solutions treated in this way show no indication of the presence of lead when analyzed by means of atomic absorption.

Ion exchangers which have become partly or completely charged with lead by purification of or removal of lead from the reaction solutions and ion exchangers which have been deliberately charged with lead ions by means of lead salt solutions may also be used as catalysts for the condensation of formaldehyde under the conditions of the process according to the present invention. It was found that these lead-charged ion exchanger resins, for example, known sulphonated polystyrene resins which are cross-linked with divinylbenzene, cross-linked acrylic acid resins or modified formaldehyde-urea derivatives, could catalyze the condensation of formaldehyde as successfully as the soluble lead salts themselves. One particular advantage of using these exchanger resins is that the quantities of lead used may be greatly reduced compared with those required in the known processes, as may be seen from Example 6. Another advantage is that these lead charged ion exchangers may be obtained directly from the desalting of the reaction solution and may be used again for desalting after they have been used as catalyst.

According to a particularly advantageous embodiment of the process of the present invention, the following procedure may be adopted when using these ion exchanger catalysts. A certain quantity of lead-charged ion exchange resin, depending on the total quantity of reaction mixture, is added to the reaction solution as solid catalyst. Lead ions are given off to the reaction solution during the reaction so that the solid catalyst is gradually depleted of lead ions. After completion of the reaction, the ion exchanger is removed by suction filtration and the reaction solution is freed from lead by passing it over an ion exchanger which is free from lead or only partly charged with lead. After repeated use, that part of the ion exchanger resin which was used as solid catalyst becomes so depleted of lead ions that it suffers some loss of catalytic activity. The other part of the ion exchanger resin, which was used for removing the lead from the solution, is now very heavily charged with lead ions. When both portions of the exchanger resin have been washed with water, only that part which was used for removing lead from the reaction solution is used as catalyst while the other part, which is now no longer completely charged with lead, is used for absorbing lead ions from the reaction mixture.

In this way, the lead required as catalyst is completely utilized and there is no need for a constant supply of fresh lead salts and no formation of harmful waste products. This embodiment of the process is therefore particularly interesting both on economical and on ecological grounds.

Another particular feature of the process according to the present invention is the use of a certain co-catalyst.

It is known from the literature that compounds which contain enediol groups or compounds which are capable of enediol formation in accordance with the following equation:

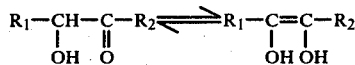

wherein
$R_1$ and $R_2$, which may be the same or different, represent hydrogen atoms, alkyl, hydroxylalkyl or aryl groups; may be used as co-catalysts for the condensation of formaldehyde. According to U.S. Pat. No. 2,224,910, the compounds used for this purpose are, in particular, glucose, ascorbic acid, fructose, benzoin, glycol aldehyde, erythrose, reductons and invert sugar. The co-catalysts are used to eliminate the period of induction at the beginning of formaldehyde condensation. However, most of these co-catalysts develop their catalytic activity only at pH values $\geq 7$, a pH range at which there is an increased in the disporportionation of formaldehyde, leading to the formation of unwanted by-products and reduction in yield. Other co-catalysts may only be prepared by complicated methods of synthesis and are therefore expensive.

It was unexpectedly found that condensation of formaldehyde hydrate could be carried out at pH values below 7 without inhibition at the beginning of the reaction if a certain mixture of hydroxyaldehydes and hydroxyketones (which may contain catalytically inactive polyhydric alcohols) of the type obtained from condensation of formaldehyde hydrate are used as co-catalysts. These co-catalysts are characterized by the following molar ratios:
Compounds having 3 carbon atoms/compounds having 4 carbon atoms from 0.5:1 to 2.0:1;
Compounds having 4 carbon atoms/compounds having 5 carbon atoms from 0.2:1 to 2.0:1;
Compounds having 5 carbon atoms/compounds having 6 carbon atoms from 0.5:1 to 5.0:1.

This co-catalyst mixture should contain at least 75%, by weight, preferably more than 85%, by weight, of components having from 3 to 6 carbon atoms.

The substance preferably used as co-catalyst is the mixture of products obtained in the process according to the present invention. This mixture generally contains the $C_3$ to $C_6$ components within the required proportions if the preferred reaction conditions indicated above are observed. On the other hand, it is, of course, possible to use mixtures of hydroxyaldehydes and hydroxyketones obtained by processes known in the art, provided the components are present in the required proportions (if necessary, the mixture may be adjusted to the required proportion of $C_3$ to $C_6$ components, for example by the addition of glyceraldehyde, erythrose, fructose or glucose). However, condensation products obtained according to the known art frequently contain impurities causing brown discoloration, as mentioned above. They must be purified before they may be used as co-catalysts in the process according to the present invention.

The known co-catalysts, for example glucose, or also ω-hydroxyacetophenone which was recognized by Langenbeck (J. pr. Ch. 3, (1956), page 196) as a particularly active co-catalyst molecular, develop their full co-catalytic activity only in the alkaline range. It is only in this pH range that inhibition of formaldehyde condensation is obviated. At pH values below 7, long induction periods at the beginning of the condensation reaction occur even in the presence of these co-catalysts, leading to low volume/time yields. The co-catalyst mixture according to the present invention, on the other hand, is capable of preventing this inhibition even at pH values below 7.

Certain known co-catalysts, such as glucose and fructose, seriously falsify the distribution of components in the resulting product mixtures. These disadvantages do not occur when using the cocatalyst mixture according to the present invention.

The quantity of co-catalyst used according to the present invention is generally from 0.1 to 50%, by weight, preferably from 0.5 to 5%, by weight, most preferably from 1 to 3%, by weight, based on the quantity of formaldehyde put into the process.

The condensation reaction proceeds so rapidly in the presence of the co-catalyst according to the present invention that the improved volume/time yields mentioned above are obtained. Since the condensation of formaldehyde to hydroxyaldehydes and hydroxyketones proceeds so rapidly at temperatures above 95° C. under the conditions according to the present invention that the reaction mixture is sufficiently heated by the heat liberated, the reaction solution need only be heated to from 90° to 100° C., whereupon the external source of heat may be removed. The quantities of heat liberated by the exothermic reaction are then so great that the reaction solution is kept boiling gently under the whole reaction time. However, the reaction velocity is sufficiently low at the given pH range to enable the reaction to be stopped at any time by external cooling or addition of acids when it is desired to do so because the required residual formaldehyde content of product distribution has been reached. The pH range employed according to the present invention is also particularly advantageous because in this range the reaction velocity may easily be controlled simply by a slight change in pH. If large quantities of heat are nevertheless produced leading to vigorous boiling, the excess heat may easily be removed by external cooling.

Inorganic bases suitable for the process according to the present invention include, for example, NaOH, KOH, CaO, Ca(OH)$_2$, MgO and Mg(OH)$_2$. Suitable organic bases include, for example, urotropine, pyridine, secondary and tertiary amines and so-called "crown ether" complexes of alkali metals.

Higher molecular weight polyols, hydroxyaldehydes and hydroxyketones (in particular, those having 5 or 6 carbon atoms) are obtained free from undesirable colored by-products by the process according to the present invention if the reaction is continued until the residual formaldehyde content has been reduced to from 0 to 1.5%, by weight, and is then stopped by cooling and/or inactivation of the catalyst. The product mixtures obtained in this way are substantially free from formaldehyde.

When the reaction is carried out in accordance with the present invention and the co-catalysts defined above are used, it is surprisingly found that the reaction is controlled so that the unwanted Cannizzaro reaction of formaldehyde with itself (disproportionation to form methanol and formic acid), which reduces the formation of hydroxyaldehydes and ketones, is substantially avoided and reactions which cause brown discoloration are prevented.

Gas chromatographic analysis of the hydrogenated and silylated reaction product shows that in the preferred embodiment of the process mentioned above (in which the reaction is continued to a residual formaldehyde content of from 0 to 1.5%, by weight) approximately 45%, by weight, of hexavalent alcohols, 25%, by weight, of pentavalent and about 20%, by weight, of heptavalent and higher valent alcohols are formed. However, only about 10% of divalent, trivalent and tetravalent alcohols are obtained (see Example 1). In the known processes for example those described in U.S. Pat. No. 2,224,910, these low molecular weight constituents amount to over 60%.

The compounds used as sources of carbohydrates, for example for feeding microorganisms, are preferably hydroxyaldehydes and hydroxyketones having 5 or 6 carbon atoms. For this reason, the mixtures of hydroxyaldehydes and hydroxyketones obtained by the process according to the present invention are preferable to the mixtures obtained by the known processes as substitutes for naturally occurring carbohydrates.

For the technical applications indicated above, it is also frequently preferred to use polyhydric alcohols having a high hydroxyl functionality of the type which may be obtained in the mixtures produced by the process according to the present invention.

However, the process according to the present invention is not restricted to the preparation of mixtures of hydroxyaldehydes or hydroxyketones and polyhydric alcohols having a predominant proportion of higher functional compounds. As indicated above, the distribution of products may be varied in accordance with the present invention by continuing the condensation reaction to a predetermined residual formaldehyde content and then stopping the reaction by cooling. If, for example, the condensation reaction is only continued to the stage when the solution still contains 8%, by weight, of free formaldehyde and the reaction mixture is then cooled, the resulting product mixture is practically free from compounds having 6 or more carbon atoms. At the same time, the proportion of compounds having 2 hydroxyl groups after reduction is increased to 16%, by weight, the proportion of compounds having 3 hydroxyl groups after reduction to 20% and the proportion of compounds having 4 hydroxyl groups (reduced form) to 30% (see Example 2).

It is therefore possible to obtain various product distributions from the process according to the present invention by continuing the condensation of formaldehyde to residual formaldehyde contents varying from 8 to 1.5%. In this way, the outcome of the process may be adjusted to any product distribution required for a given purpose.

The condensation reaction according to the present invention may be carried out particularly advantageously in a continuous cascade of stirrer vessels. In this embodiment of the process, the residual formaldehyde content may be exactly adjusted by varying the residence time in the individual stirrer vessels. The distribution of products in the reaction mixture and the average hydroxyl functionality of the mixture of polyhydric alcohols obtained by reduction of the reaction mixture are therefore easily variable within wide limits and are reproducible.

The preparation of a mixture of hydroxyl compounds by the process according to the present invention may be carried out equally successfully in a continuously operating reaction tube. In this case, the whole reaction volume may be maintained at a desired pH by continuously adding the necessary quantity of inorganic or organic base at several points along the tube. Here again, the product distribution and hydroxyl functionality of the resulting polyhydric alcohols may be varied within wide limits by varying the rates of flow through the reactor. This embodiment of the process is, of course, also suitable for producing mixtures containing predominantly higher molecular weight compounds free from colored by-products.

Mixtures consisting predominantly of higher molecular weight products are also obtained when hydroxyaldehyde and hydroxyketone mixtures consisting mainly of low molecular weight components are post-treated with excess formaldehyde in the presence of an inorganic or organic base at a pH of from 9 to 13, preferably from 10 to 11, for periods ranging from 10 minutes to 12 hours at temperatures of from 10° to 100° C., preferably from 30° to 60° C. This method not only converts low molecular weight compounds into higher molecular weight compounds by an alkaline-catalyzed aldol reaction, but also increases the formation of branched hydroxyaldehydes and hydroxyketones by additional methylolation on the carbon atom adjacent to the carbonyl group. These branched hydroxyketones and hydroxyaldehydes contain a substantially higher proportion of primary hydroxyl groups than the corresponding straight-chain compounds. The reactivity of these mixtures towards compounds which are reactive with hydroxyl groups is thereby considerably increased, a factor which is an advantage for some purposes. Thus, for example, when compounds prepared according to the present invention are reacted with organic isocyanates, the presence of primary OH groups causes a much more rapid formation of urethane groups than is obtained with normal, straight-chain polyhydric alcohols containing secondary OH groups.

The hydroxyaldehydes and hydroxyketones obtained by the process according to the present invention may, if desired, easily be reduced to polyhydric alcohols by known methods. Thus, for example, direct reduction of the aqueous solution obtained from the process may be carried out at room temperature using sodium borohydride, but for example, it may also be carried out electrolytically. Catalytic hydrogenation with hydrogen is another possible method. Any procedures conventionally employed for the reduction of sugars to sugar alcohols may be employed for this method. Hydrogenation with Raney nickel in quantities of from 5 to 20%, by weight, based on the hydroxyaldehyde and hydroxyketone mixtures which is required to be reduced, at hydrogen pressures of from 50 to 200 kg/cm² and temperatures of from 20° to 200° C. is particularly advantageous. However, catalysts containing nickel, cobalt, copper, platinum, rhodium or palladium on inert carriers may be used with equal success.

The method of carrying out the reaction in accordance with the present invention has the result that practically no decomposition products which would interfere with hydrogenation are formed. In particular, there is no formation of carboxyl compounds, such as lactic acid or saccharic acids, which would reduce the activity of hydrogenation catalysts which are unstable in the presence of acids. The hydrogenation catalysts may therefore be used repeatedly without loss of activity in the hydrogenation of the mixtures of hydroxyaldehydes, hydroxyketones and polyhydric alcohols prepared in accordance with the present invention.

As described above, it is possible to regulate the process according to the present invention by suitable control of the pH. A high proportion of the hydroxyaldehydes and hydroxyketones formed in the reaction is reduced to polyhydric alcohols in situ by the formaldehyde present in the reaction mixture. Alternatively, the hydroxyaldehydes and hydroxyketones (which are formed to an increased extent if the pH lies slightly outside the preferred range) may be reduced subsequently using formaldehyde. For this purpose, excess formaldehyde and an inorganic base are added to the reaction solution and the solution is stirred for a period varying from 30 minutes to 12 hours at from 10° to 100° C., preferably from 30° to 60° C., at a pH of from 9 to 13, preferably from 10 to 11. By this procedure it is possible not only to reduce the carbonyl function, but at the same time, as mentioned above, to synthesize higher molecular weight and branched products. Preferred inorganic bases which accelerate the crossed Cannizzaro reaction include: sodium hydroxide, potassium hydroxide, calcium and barium hydroxides and the so-called "crown ether" complexes of alkali metals.

The reducing reaction may be further accelerated by co-catalysts. Preferred co-catalysts for this purpose include: oxalates of transition metals, in particular nickel, cobalt, iron, cadmium, zinc, chromium and manganese oxalate, and transition metals in the form of the element, e.g. nickel, cobalt, iron copper, cadmium, zinc, chromium and manganese. Activated nickel used in the form of so-called "Raney nickel" and elementary zinc in powder form are particularly preferred.

Other co-catalysts which may be used for reduction using formaldehyde include: amides of organic acids, such as formamide, dimethylformamide and acetamide, and tetraalkyl ammonium salts, in particular tetramethylammonium chloride, and tetraethylammonium chloride.

It may be economically particularly advantageous to carry out the process according to the present invention immediately after the production of formaldehyde and make use of the heat stored in the formaldehyde vapor. For example, one commonly used commercial process for the production of formaldehyde, operates according to the following reaction equation:

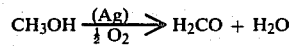

In this process the reaction products are so vigorously heated by the exothermic reaction that they are obtained in the gaseous form.

Summarizing, it is found that the process according to the present invention affords the following major advantages over the processes known in the art:

1. The process according to the present invention produces mixtures of hydroxyaldehydes, hydroxyketones and polyhydric alcohols in which the proportion of polyhydric alcohols (produced by the crossed Cannizzaro reaction) is from 30 to 75%, by weight, and which are free from undesirable decomposition products. Hydrogenation or reduction of these mixtures may be carried out very economically and simply since only relatively small quantities of carbonyl groups have to be converted into hydroxyl functions.

2. The process according to the present invention produces mixtures of polyols, hydroxyaldehydes and hydroxyketones having differing OH-functionalities, the distribution of which in the mixture may be controlled and varied as desired for a particular purpose. In particular, it is possible to produce mixtures containing more than 90%, by weight, of compounds which have more than 4 carbon atoms. The high reproducibility of the distribution of products also constitutes a major advantage over the processes known in the art.

3. The process according to the present invention gives rise to colorless products which may be directly hydrogenated or put to use for any of the other purposes described without first being purified. It is not necessary to work-up the product mixtures by distillation.

4. The process according to the present invention is very economical compared with the processes known in the art. The use of highly concentrated formaldehyde solutions saves the energy costs which would be required for evaporating solvent. Since practically no unwanted side reactions occur in the process according to the present invention, yields of from 95 to 98%, based on the quantity of formaldehyde put into the process, are attained.

Compared with the known processes of the art, the process according to the present invention is very rapid and extremely high volume/time yields are therefore obtainable.

5. The lead catalysts used in the process according to the present invention may be reused, either immediately or after a simple step of regeneration, so that no lead waste which would be ecologically harmful is formed.

The mixtures of hydroxyaldehydes and hydroxyketones obtainable according to the present invention and the polyhydric alcohols obtained therefrom by crossed Cannizzaro reaction or by hydrogenation are valuable starting materials for numerous products which have important technical applications.

For example, the polyhydroxyl compounds obtained by reduction are very suitable for use as chain lengthening agents or cross-linking agents in the production of polyurethane resins from polyisocyanates, low molecular weight polyhydroxyl compounds and optionally higher molecular weight polyhydroxyl compounds, other chain lengthening agents, blowing agents, catalysts and other known additives.

The polyisocyanates used for this purpose may be, for example, the aliphatic, cycloaliphatic, araliphatic, aromatic or heterocyclic polyisocyanates described, by W. Siefken in Justus Liebigs Annalen der Chemie, 562, pages 75 to 136. These include ethylene diisocyanate; tetramethylene-1,4-diisocyanate; hexamethylene-1,6-diisocyanate; dodecane-1,12-diisocyanate; cyclobutane-1,3-diisocyanate; cyclohexane-1,3- and -1,4-diisocyanate and mixtures of these isomers; 1-isocyanato-3,3,5-trimethyl-5-isocyanatomethyl-cyclohexane (German Auslegeschrift 1,202,785, U.S. Pat. No. 3,401,190), hexahydrotolylene-2,4-diisocyanate and -2,6-diisocyanate and mixtures of these isomers; hexahydrophenylene-1,3-diisocyanate and/or 1,4-diisocyanate; perhydrodiphenylmethane-2,4'-diisocyanate and/or 4,4'-diisocyanate; phenylene-1,3-diisocyanate and -1,4-diisocyanate; tolylene-2,4-diisocyanate and -2,6-diisocyanate and mixtures of these isomers; diphenylmethane-2,4'-diisocyanate; and/or 4,4'-diisocyanate; naphthylene-1,5-diisocyanate; triphenylmethane-4,4',4"-triisocyanate; polyphenyl-polymethylene polyisocyanates which may be obtained by aniline-formaldehyde condensation followed by phosgenation and which have been described, for example, in British Pat. Nos. 874,430 and 848,671; m- and p-isocyanatophenylsulphonyl isocyanates according to U.S. Pat. No. 3,454,606; perchlorinated aryl polyisocyanates, such as those described, for example, in German Auslegeschrift No. 1,157,601 (U.S. Pat. No. 3,277,138); polyisocyanates having carbodiimide groups as described in German Pat. No. 1,092,007 (U.S. Pat. No. 3,152,162); diisocyanates of the type described in U.S. Pat. No. 3,492,330; polyisocyanates containing allophanate groups as described, e.g. in British Pat. No. 994,890, in Belgian Pat. No. 761,626 and in published Dutch patent application No. 7,102,524; polyisocyanates containing isocyanurate groups, e.g. as described in U.S. Pat. No. 3,001,973, in German Pat. Nos. 1,022,789; 1,222,067 and 1,027,394 and in German Offenlegungsschriften Nos. 1,929,034 and 2,004,048; polyisocyanates containing urethane groups as described, e.g. in Belgian Pat. No. 752,261 or in U.S. Pat. No. 3,394,164; polyisocyanates containing acylated urea groups according to German Pat. No. 1,230,778; polyisocyanates containing biuret groups as described, e.g. in German Pat. No. 1,101,394, (U.S. Pat. Nos. 3,124,605 and 3,201,372) and in British Patent 889,050; polyisocyanates prepared by telomerization reactions as described, for example, in U.S. Pat. No. 3,654,106; polyisocyanates having ester groups, such as those mentioned, for example, in British Pat. Nos. 965,474 and 1,072,956, in U.S. Pat. No. 3,567,763 and in German Pat. No. 1,231,688; reaction products of the above-mentioned isocyanates with acetals according to German Pat. No. 1,072,385 and polyisocyanates containing polymeric fatty acid groups according to U.S. Pat. No. 3,455,883.

The distillation residues obtained from the commercial production of isocyanates and still containing isocyanate groups may also be used, optionally as solutions in one or more of the above-mentioned polyisocyanates. Mixtures of the above-mentioned polyisocyanates may also be used.

As a general rule, it is particularly preferred to use commercially readily available polyisocyanates, such as tolylene-2,4-diisocyanate and -2,6-diisocyanate and mixtures of these isomers ("TDI"), polyphenyl-polymethylene polyisocyanates of the type which may be prepared by anilineformaldehyde condensation followed by phosgenation ("crude MDI") and polyisocyanates containing carbodiimide groups, urethane groups, allophanate groups, isocyanurate groups, urea groups or biuret groups ("Modified polyisocyanates").

Suitable higher molecular weight polyhydroxyl compounds, especially those having a molecular weight of from 800 to 10,000 preferably from 1000 to 6000. These include, e.g. polyesters, polyethers, polythioethers, polyacetals, polycarbonates and polyester amides having at least 2, generally from 2 to 8, but preferably from 2 to 4 hydroxyl groups, of the type known for the production of both homogeneous and cellular polyurethanes.

Suitable polyesters containing hydroxyl groups include, e.g. reaction products of polyhydric, preferably dihydric alcohols, optionally with the addition of trihydric alcohols, and polybasic, preferably dibasic, carboxylic acids. Instead of free polycarboxylic acids, the corresponding polycarboxylic acid anhydrides or corresponding polycarboxylic acid esters of lower alcohols or mixtures thereof may, of course, be used for preparing the polyesters. The polycarboxylic acids may be aliphatic, cycloaliphatic, aromatic and/or heterocyclic and they may be substituted, e.g. by halogen atoms, and/or may be unsaturated.

The following are mentioned as examples: Succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids, such as oleic acid, optionally mixed with monomeric fatty acids, dimethyl terephthalate and terephthalic acid-bis-glycol esters. The following are examples of suitable polyhydric alcohols: ethylene glycol, propylene glycol-(1,2) and —(1,3), butylene glycol-(1,4) and —(2,3), hexanediol-(1,6), octanediol-(1,8), neopentylglycol, cyclohexanedimethanol (1,4-bis-hydroxymethylcyclohexane), 2-methyl-1,3-propanediol, glycerol, trimethylolpropane, hexanetriol-(1,2,6), butanetriol-(1,2,4), trimethylolethane, pentaerythritol, quinitol, mannitol and sorbitol, methylglycoside, diethylene glycol, triethylene glycol, tetraethylene glycol, higher polyethylene glycols, dipropylene glycol, higher polypropylene glycols, dibutylene glycol and higher polybutylene glycols. The polyesters may also contain a proportion of carboxyl end groups. Polyesters of lactones, such as $\epsilon$-caprolactone, or hydroxycarboxylic acids, such as $\omega$-hydroxycaproic acid, may also be used.

The polyethers which may be used according to the present invention, which have at least 2, generally from 2 to 8, preferably 2 or 3, hydroxyl groups, are also known. They are prepared, for example, by the polymerization of epoxides, such as ethylene oxide, propylene oxide, butylene oxide, tetrahydrofuran, styrene oxide or epichlorohydrin, either each on its own, e.g. in the presence of $BF_3$, or by addition of these epoxides, optionally as mixtures of successively, to starting components having reactive hydrogen atoms. Such starting compounds include water, ammonia, alcohols or amines, e.g. ethylene glycol, propylene glycol-(1,3) or -(1,2), trimethylolpropane, 4,4'-dihydroxydiphenylpropane, aniline, ethanolamine or ethylene diamine. Sucrose polyethers may also be used according to the present invention, e.g. those described in German Auslegeschriften Nos. 1,176,358 and 1,064,938. It is in many cases preferred to use polyethers which contain predominantly primary OH groups (up to 90%, by weight, based on all the OH groups present in the polyether). Polyethers modified with vinyl polymers, e.g. the compounds obtained by polymerization of styrene and acrylonitrile in the presence of polyethers (U.S. Pat. Nos. 3,383,351; 3,304,273; 3,523,093 and 3,110,695 and German Pat. No. 1,152,536) are also suitable, as well as polybutadienes which have OH groups.

Particularly to be mentioned among the polythioethers are the condensation products obtained by reacting thiodiglycol on its own and/or with other glycols, dicarboxylic acids, formaldehyde, aminocarboxylic acids or amino alcohols. The products obtained are polythio mixed ethers, polythio ether esters or polythioether ester amides, depending on the co-components.

Suitable polyacetals include, for example, the compounds which may be prepared from glycols, such as diethylene glycol, triethylene glycol, 4,4'-dioxethoxydiphenyl dimethylmethane and hexanediol, by reaction with formaldehyde. Suitable polyacetals for the purposes of the present invention may also be prepared by the polymerization of cyclic acetals.

The polycarbonates containing hydroxyl groups used may be of the type known, for example those which may be prepared by the reaction of diols, such as propanediol-(1,3), butanediol-(1,4) and/or hexanediol-(1,6), diethylene glycol, triethylene glycol or tetraethylene glycol, with diarylcarbonates, e.g. diphenylcarbonate, or with phosgene.

Suitable polyester amides and polyamides include, for example, the predominantly linear condensates prepared from polybasic saturated and unsaturated carboxylic acids or the anhydrides thereof and polyfunctional saturated and unsaturated amino alcohols, diamines, polyamines and mixtures thereof.

Polyhydroxyl compounds already containin urethane or urea groups and modified or unmodified natural polyols, such as castor oil, or carbohydrates such as starch may also be used. Addition products of alkylene oxides and phenolformaldehyde resins or of alkylene oxides and urea-formaldehyde resins are also suitable for the purposes of the present invention.

Representatives of these compounds which may be used according to the present invention have been described, for example, in High Polymers, Vol. XVI, "Polyurethanes, Chemistry and Technology" by Saunders-Frisch, Interscience Publishers, New York, London, Volume I, 1962, pages 32–42 and pages 44–54 and Volume II, 1964, pages 5–6 and 198–199 and in Kunststoff-Handbuch, Volume VII, Vieweg-Höchtlen, Carl-Hanser-Verlag, Munich, 1966, e.g. on pages 45 to 71.

Mixtures of the above-mentioned compounds which contain at least two hydrogen atoms capable of reacting with isocyanates and have a molecular weight of from 800 to 10,000 may, of course, also be used, for example mixtures of polyethers and polyesters.

The starting components which may be used according to the present invention may also include compounds having a molecular weight of from 32 to 400 which have at least two hydrogen atoms capable of reacting with isocyanates. These compounds are also understood to be compounds containing hydroxyl groups and/or amino groups and/or thiol groups and/or carboxyl groups, preferably hydroxyl groups and/or amino groups. They serve as chain-lengthening agents or crosslinking agents. They generally have from 2 to 8 hydrogen atoms capable of reacting with isocyanates, preferably 2 or 3 such hydrogen atoms.

The following are examples of such compounds: ethylene glycol, propylene glycol-(1,2) and -(1,3), butylene glycol-(1,4) and -(2,3), pentanediol-(1,5), hexanediol-(1,6), octanediol-(1,8), neopentyl glycol, 1,4-bis-hydroxymethylcyclohexane, 2-methyl-1,3-propanediol, glycerol, trimethylol propane, hexanetriol-(1,2,6), trimethylolethane, pentaerythritol, quinitol, mannitol and sorbitol, diethylene glycol, triethylene glycol, tetraethylene glycol, higher polyethylene glycols having a molecular weight of up to 400, dipropylene glycol, higher polypropylene glycols having a molecular weight of up to 400, dibutylene glycol, higher polybutylene glycols having a molecular weight of up to 400, 4,4'-dihydroxydiphenyl propane, dihydroxymethyl-hydroquinone, ethanolamine, diethanolamine, triethanolamine, 3-aminopropanol, ethylene diamine, 1,3-diaminopropane, 1-mercapto-3-aminopropane, 4-hydroxyphthalic acid, 4-aminophthalic acid, succinic acid, adipic acid, hydrazine, N,N-dimethylhydrazine, 4,4'-diaminodiphenylmethane, tolylene diamine, methylene bis-chloroaniline, methylene-bis-anthranilic acid esters, diaminobenzoic acid esters and the isomeric chlorophenylene diamines.

In this case again there may be used mixtures of various compounds having a molecular weight of from 32 to 400 and containing at least two hydrogen atoms capable of reacting with isocyanates.

Polyhydroxyl compounds in which high molecular weight polyadducts or polycondensates are contained in a finely dispersed or dissolved form may also be used according to the present invention. These modified polyhydroxyl compounds are obtained when polyaddition reactions (e.g. reactions between polyisocyanates and aminofunctional compounds) or polycondensation reactions (e.g. between formaldehyde and phenols and/or amines) are carried out in situ in the abovementioned hydroxyl compounds. Such processes have been described, for example, in German Auslegeschriften No. 1,168,075 and 1,260,142 and in German Offenlegungsschriften Nos. 2,234,134; 2,423,984; 2,512,385; 2,513,815; 2,550,796; 2,550,797, 2,550,833 and 2,550,862. Modified polyhydroxyl compounds of this type may also be obtained by mixing a previously prepared aqueous polymer dispersion with a polyhydroxyl compound and then removing water from the mixture in accordance with U.S. Pat. No. 3,869,413 or German Offenlegungsschrift No. 2,550,860.

When modified polyhydroxyl compounds of the type indicated above are used as starting components in the polyisocyanate polyaddition process, polyurethane resins having substantially improved mechanical properties are obtained in many cases.

When the polyhydroxyl compounds obtainable according to the present invention are reacted exclusively with highly elastified polyisocyanates, such as polyisocyanates having a biuret structure (German Auslegeschrift No. 1,543,178), that is to say without the addition of other components which are reactive with isocyanates, the products are coating and lacquers which are light-fast, scratch-resistant and solvent-resistant.

Polyether alcohols of high functionality may be obtained by propoxylation and/or ethoxylation of the polyols. The polyether alcohols having high OH numbers are suitable for the production of rigid or semi-rigid cellular polyurethane resins and those having low OH numbers may be used as starting materials for highly elastic polyurethane foams.

Highly cross-linked polyesters which may be used as additives to alkyd resins to improve their hardness are obtained when the above-described mixtures of polyhydric alcohols prepared according to the present invention and polybasic carboxylic acids, such as phthalic acid, isophthalic acid, terephthalic acid, tetra- and hexahydrophthalic acid, adipic acid or maleic acid, are reacted by the conventional methods of polyester condensation, for example the methods described in Houben-Weyl, Methoden der organischen Chemie, Vol. XIV 12, page 40. Hydroxyl polyesters synthesized from the hydroxyl compounds prepared according to the present invention may, of course, also be used as starting components for the production of polyurethane resins.

The polyhydric alcohols prepared according to the present invention, as well as the hydroxyaldehydes and hydroxyketones may also be reacted very easily with long-chain aliphatic monocarboxylic acids, such as caprylic, capric, lauric, myristic, palmitic, stearic, oleic, linoleic, arachidonic or behenic acid and derivatives thereof, e.g. their methyl or ethyl esters or anhydrides or mixed anhydrides, to produce esters containing hydroxyl groups. These esters as well as the ethoxylation products of the polyols according to the invention and the carbamic acid esters obtained as reaction products of the polyhydroxyl compounds obtained according to the present invention with long chain monoisocyanates, such as n-octyl, n-decyl, n-dodecyl, myristyl, cetyl or stearyl isocyanate (see, for example, K. Lindner, Tenside Volume III, Wissenschaftliche Verlagsgesellschaft Stuttgart, 1964, page 2336), are non-ionogenic surface active compounds which are valuable emulsifiers, wetting agents or plasticizers. The compounds according to the present invention may also be used as moisture-retaining agents in cosmetics and synthetic resins. They may also be used, for example, as anti-freezes.

They may also be used as carbohydrate-containing substrates in the nutrient media of microorganisms. Products consisting mostly of hydroxyaldehyde and hydroxyketones having 5 or 6 carbon atoms have proved to be particularly suitable for this purpose.

The following Examples serve to illustrate the process according to the present invention. (The figures given represent parts, by weight, or percentages, by weight, unless otherwise indicated.)

EXAMPLE 1

30,000 Parts of a 37% aqueous formaldehyde solution (370 mol of formaldehyde) are heated to from 70° to 90° C. 150 Parts (0.4 mol) of lead(II) acetate and 810 parts of a 37% aqueous solution of a co-catalyst mixture which has been prepared by a method of formaldehyde condensation analogous to that of German Pat. No. 884,794, as will be described below, (with pH control in accordance with the present invention) and in which the molar ratio of compounds having 3 carbon atoms: compounds having 4 carbon atoms is 0.75:1, the molar ratio of compounds having 4 carbon atoms: compounds having 5 carbon atoms is 0.23:1 and the molar ratio of compounds having 5 carbon atoms: compounds having 6 carbon atoms is 0.67:1, are added at this temperature. The mixture is then heated to from 90° to 95° C. and the external heating means removed when this temperature is reached. During the next 5 minutes, the pH of the solution is adjusted to 6.5 by the addition of approximately 2000 parts of a 10% potassium hydroxide solution. During the exothermic reaction which sets in at once, the reaction temperature rises to from 98° to 99° C. and the reaction mixture begins to boil. The pH is maintained at 6.5 by steady dropwise addition of KOH solution until 30% of the starting material has reacted (formaldehyde content of the reaction mixture: 23.6%). At that stage, the addition of KOH is stopped so that the pH of the mixture slowly drops. When the pH has fallen to 5.7, it is maintained at this level by dropwise addition of a further 700 parts of potassium hydroxide solution to the gently boiling reaction mixture. The formaldehyde content has dropped to 16% after 20 minutes, to 13% after 25 minutes and to 8% after 30 minutes. After a further 10 minutes, the reaction mixture contains only 1.3% of formaldehyde. The reaction is then stopped by cooling. When the temperature of the reaction mixture has dropped to 90° C., 50 parts of active charcoal are added. 100 Parts of potassium carbonate are added at 65° C. to precipitate the lead ions. After removal of the precipitated lead carbonate and the active charcoal by filtration, a clear, colorless solution is obtained, from which 11,713 parts of a colorless, viscous mixture of polyhydric alcohols, hydroxyaldehydes and hydroxyketones containing 9.8% of water are obtained by evaporation under a water jet vacuum at 40° C. A mixture of polyhydric alcohols is obtained from this mixture of polyhydric alcohols, hydroxyaldehydes and hydroxyketones by electrochemical reduction or catalytic hydrogenation (see Example 10). Gas chromatographic analysis of the silylized polyhydric alcohols shows the following distribution of components:
dihydric alcohols—0.2%, by weight,
trihydric alcohols—2.6% by weight,
tetrahydric alcohols—4.6%, by weight,
pentahydric alcohols—24.8%, by weight,
hexahydric alcohols—44.5%, by weight,
heptahydric alcohols and higher hydric alcohols—23.5%, by weight.

Preparation of the co-catalyst

3000 Parts of a 37% aqueous formaldehyde solution (37 mol of formaldehyde) are heated to from 70° to 90° C. 30 Parts (0.08 mol) of lead(II) acetate are added at this temperature. The mixture is then heated to 100° C. and adjusted to a pH of 6.7 at this temperature by dropwise addition of a 15% suspension of Ca(OH)$_2$.

After 6 hours, the formaldehyde content has dropped to 20% and the addition of Ca(OH)$_2$ is stopped at this stage. The pH of the reaction mixture then falls only slowly. When the pH has dropped to 5.7, it is maintained at this level by further addition of Ca(OH)$_2$ suspension to the mixture. After a further 7.5 hours, the residual formaldehyde content has dropped to 0.5% and the reaction mixture is cooled. An approximately 37% solution of a co-catalyst mixture consisting of hydroxyaldehydes and hydroxyketones is obtained, in which the molar ratio of compounds having 3 carbon atoms: compounds having 4 carbon atoms is 0.75:1, the molar ratio of compounds having 4 carbon atoms: compounds having 5 carbon atoms is 0.23:1 and the molar ratio of compounds having 5 carbon atoms: compounds having 6 carbon atoms is 0.67:1. This solution is immediately ready for use as co-catalyst.

EXAMPLE 2

This Example illustrates how the distribution of products in the resulting polyol mixture may be altered by stopping formaldehyde condensation at an earlier stage (at a residual formaldehyde content of approximately 8%, by weight).

150 Parts (0.4 mol) of lead(II) acetate and 810 parts of a 37% aqueous solution of the mixture of hydroxyaldehydes, hydroxyketones and polyhydric alcohols described in Example 1, which serves as co-catalyst, are added to 30,000 parts (370 mol) of a 37% aqueous formaldehyde solution as described in Example 1 and the reaction mixture is condensed to a mixture of polyhydroxyl compounds by the method described in Example 1. When the formaldehyde content has dropped to 8%, by weight, (30 minutes after addition of potassium hydroxide solution), the reaction is stopped by cooling. The solution is freed from lead by precipitation with potassium carbonate. The clear, colorless solution obtained after filtration is hydrogenated and worked-up as described in Example 10. Gas chromatographic analysis of the polyhydric alcohol mixture obtained shows the following distribution of components:

dihydric alcohols: 16.8%, by weight,
trihydric alcohols: 21.0%, by weight,
tetrahydric alcohols: 29.9%, by weight,
pentahydric alcohols: 25.1%, by weight,
hexahydric alcohols: 7.2%, by weight,
heptahydric alcohols: 0.0%, by weight.

EXAMPLE 3

7000 Parts of a 37% aqueous formaldehyde solution (86 mol of formaldehyde) are heated to from 70° to 90° C. At this temperature there are added 25 parts of lead-(II) oxide (about 0.1 mol) and 190 parts of a 37% solution of a mixture of hydroxyaldehydes, hydroxyketones and polyhydric alcohols serving as co-catalyst. This co-catalyst mixture was prepared, as described in Example 1, by formaldehyde condensation in accordance with German Pat. No. 884,794 and in this mixture the molar ratio of compounds having 3 carbon atoms: compounds having 4 carbon atoms is 0.56:1, the molar ratio of compounds having 4 carbon atoms: compounds having 5 carbon atoms is 0.52:1 and the molar ratio of compounds having 5 carbon atoms: compounds having 6 carbon atoms is 1.34:1. On addition of this mixture of lead acetate and this co-catalyst, the pH of the formaldehyde solution rises from 3.8 to 6.9. The lead oxide dissolves in the reaction mixture within a few minutes and a clear, homogeneous solution is obtained. The reaction is then continued as described in Example 1 and stopped by cooling when the residual formaldehyde content is 7.8%, by weight. The solution is freed from lead by precipitation with potassium carbonate. The clear, colorless solution left after filtration is hydrogenated and worked-up as described in Example 10. Gas chromatographic analysis shows that the polyhydric alcohol mixture obtained has the following distribution of components:

dihydric alcohols: 17.5%, by weight,
trihydric alcohols: 24.9%, by weight,
tetrahydric alcohols: 31.4%, by weight,
pentahydric alcohols: 14.3%, by weight,
hexahydric alcohols: 1.9%, by weight.

EXAMPLE 4

7000 Parts of a 37% aqueous formaldehyde solution are heated to 70° C. (86 mol of formaldehyde). 25.8 parts of basic lead carbonate (0.03 mol) and 190 parts of a 37% solution of co-catalyst from Example 3 are added at this temperature. After from 10 to 15 minutes, the basic lead carbonate has gone into solution and the reaction mixture has become clear and homogeneous. The reaction is then continued as described in Example 1. 45 Minutes after addition of the potassium hydroxide solution, the residual formaldehyde content has dropped to 0.5% and the reaction is stopped by cooling. To remove the ionic constituents, the reaction mixture is passed over a commercial cation exchanger (polystyrene resin containing sulphonic acid groups) in the hydrogen ion form and then over an anion exchanger in the hydroxyl ion form. Concentration by evaporation in a water jet vacuum yields 2520 parts of a colorless, viscous mixture of hydroxyaldehydes, hydroxyketones and polyhydric alcohols containing 6% of water.

EXAMPLE 5

This Example illustrates the use of lead-charged ion exchangers as catalysts for formaldehyde self-condensation.

(A) Preparation of the lead-charged ion exchanger: An aqueous solution of lead(II) acetate is pumped over 500 parts of an ion exchanger which contains sulphonic acid groups and is based on polystyrene cross-linked with divinylbenzene and has a total capacity of 1.9 milliequivalents/ml of swelled resin. This operation is continued until the lead concentration of the eluate is equal to that of the starting solution and the ion exchanger has been completely charged with lead ions. The exchanger is then washed with deionized water until no lead ions may be detected in the eluate.

(B) Process according to the present invention: 40 Parts, by volume, of moist ion exchanger resin which has been charged with a total of 8.3 parts (0.04 mol) of lead as described above and 81 parts of a 37% aqueous solution of the co-catalyst from Example 1 are added to 3000 parts of a 37% aqueous formaldehyde solution (37 mol of formaldehyde) at 70° C. The reaction mixture is then treated as described in Example 1. The reaction mixture is cooled after 45 minutes when the formaldehyde content is still 1.0%. The reaction mixture is worked-up as described in Example 1 and 1160 parts of a colorless, viscous mixture of hydroxyaldehydes, hydroxyketones and polyhydric alcohols having a water content of 8.4% are obtained.

EXAMPLE 6

405 parts of a 37% formaldehyde solution (5 mol of formaldehyde) are reacted as described in Example 5 in the presence of 24.9 parts of a polymethyleneurea which has been modified with acid groups according to German Offenlegungsschrift No. 2,324,134 and charged with 0.4% of lead(II) ions (0.1 part of lead). After 70 minutes, the formaldehyde content of the solution has dropped to 0.5% and the reaction is stopped by cooling. The reaction mixture is freed from salt by passing it over a cation exchanger in the hydrogen ion form and then over an anion exchanger in the hydroxyl ion form and concentrated by evaporation in a water jet vacuum at 40° C. 141 g of a colorless, salt-free, viscous product having a water content of 4.5% are obtained.

EXAMPLE 7

3000 Parts of a 37% formaldehyde solution are reacted by the method described in Example 1 to form a mixture of polyhydric alcohols and hydroxyketones having the following distribution of components:

$C_2$ compounds—0.5%, by weight,
$C_3$ compounds—3.1%, by weight,
$C_4$ compounds—6.2%, by weight,
$C_5$ compounds—24.1%, by weight,
$C_6$ compounds—44.9%, by weight,
$C_7$ compounds—21.2%, by weight.

Determination of the proportion of reduced constituents in the product mixture (sugar determination using Fehling's solution) shows a sugar content, calculated as glucose, of 50.5%, and a molecular weight of 180. On the basis of the distribution of components indicated above, the mixture synthesized in this Example is calculated from these figures to have an average molecular weight of 165. If the proportion of reduced components is converted to this average molecular weight, the product mixture is found to contain about 53.7% of polyhydric alcohols.

EXAMPLE 8

500 Parts of a 30% aqueous formaldehyde solution (5 mol of formaldehyde) are heated to from 70° to 90° C. and reacted with lead(II) acetate and a solution of the co-catalyst from Example 1 by a method analogous to that of Example 1. The pH of the solution is adjusted to 7.0 by dropwise addition of a 50% sodium hydroxide solution. 10 Minutes after the addition of sodium hydroxide solution has begun, the reaction solution still contains 17%, by weight, of formaldehyde. Addition of the 50% sodium hydroxide solution is stopped at this stage. The pH of the solution thereafter falls slowly. When the pH of the reaction mixture has dropped to 5.7, it is maintained at this level by the addition of small quantities of 50% sodium hydroxide solution until the formaldehyde content has been reduced to 0.5%, by weight. The reaction is then stopped by cooling and the reaction mixture is freed from salt and worked-up as described in Example 4. Determination of the proportion of reduced components in the resulting product indicates a sugar content of 27.8%, calculated as glucose, or 25.4%, based on an average molecular weight of 165. The product mixture therefore contains about 75% of polyhydric alcohols.

EXAMPLE 9

130 g of Raney nickel are added to 7000 g of the colorless, lead-free solution of polyhydric alcohols, hydroxyaldehydes and hydroxyketones prepared according to Example 1. The solution is hydrogenated at a hydrogen pressure of 200 kp/cm² at room temperature until no more hydrogen is taken up. The temperature is then slowly raised to 160° C. in several steps while hydrogenation is continued. Hydrogenation is terminated after a total hydrogenation time of from 6 to 10 hours. A colorless, clear solution is obtained after filtration from the catalyst. Concentration of this solution by evaporation under vacuum yields 2230 g of a viscous mixture of polyhydric alcohols. The mixture is colorless and unreactive to Fehling's solution. It is not discolored brown by boiling with alkalies.

EXAMPLE 10

400 g of the mixture of polyhydric alcohols from Example 9 having the distribution of components indicated in Example 1 are dehydrated in a water jet vacuum at 130° C. 1600 g of dimethyl formamide and 562 g of methyl stearate are added to the anhydrous mixture. 70 g of a 30% sodium methylate solution are then added dropwise at room temperature and the mixture is stirred at from 95° to 100° C. and 180 bar until no more methanol distills off.

When dimethylformamide is removed by distillation, a waxy mass is left behind, which is freed from excess polyhydricalcohols by treatment with hot water. The aqueous slurry is pressed to remove excess water and dried under vacuum. A white, waxy mass which has good surface active properties is obtained.

EXAMPLE 11

200 g of the mixture of polyhydric alcohols described in Example 1 are dehydrated as indicated in Example 10 and 0.5 g of triethylene diamine is added. The mixture is heated to 100° C. 281 g of stearyl isocyanate are added dropwise at this temperature over a period of 40 minutes and the mixture is stirred until no more isocyanate may be detected by IR spectroscopy. A waxy product which has good surface active properties is obtained on cooling.

What is claimed is:

1. In a process for the preparation of mixtures of low molecular weight polyhydroxyl compounds and hydroxyl aldehydes and hydroxy ketones by condensation of formaldehyde in the presence of compounds of divalent lead as catalysts and in the presence of co-catalysts containing a mixture of hydroxy aldehydes and hydroxy ketones, at a reaction temperature of from 70° to 110° C., the improvement which comprises
   (1) condensing aqueous formalin solutions and/or paraformaldehyde dispersions containing from 20 to 65% by weight of formaldehyde in the presence of:
      (a) soluble or insoluble lead (II) salts or divalent lead attached to a high molecular weight resinous carrier; and
      (b) a co-catalyst comprising a mixture of hydroxy aldehydes and hydroxy ketones obtainable by condensation of formaldehyde, which mixture contains at least 75% by weight of $C_3$–$C_6$-compounds and is characterized by the following molar ratios:
   compounds having 3 carbon atoms/compounds having 4 carbon atoms from 0.5:1 to 2.0:1;
   compounds having 4 carbon atoms/compounds having 5 carbon atoms from 0.2:1 to 2.0:1;
   compounds having 5 carbon atoms/compounds having 6 carbon atoms from 0.5:1 to 5.0:1;
   (2) maintaining the pH of the reaction solution at from 6.0 to 7.0 by controlled addition of inorganic or organic base until from 10 to 60% by weight of the starting material has undergone reaction,
   (3) thereafter, lowering the pH of the reaction solution by from 0.5 to 3.0 units to a pH of from 4 to 6,
   (4) continuing the reaction at a pH of from 4.0 to 6.0, and
   (5) stopping the self-condensation of formaldehyde hydrate by cooling and/or by inactivation of the lead catalyst by means of acids when the residual formaldehyde content in the reaction mixture is from 0 to 10% by weight of formaldehyde and thereafter removing the catalyst in the known manner.

2. The process of claim 1 wherein the catalysts containing divalent lead are ion exchangers charged with divalent lead ions.

3. The process of claim 1 wherein formaldehyde condensation is carried out continuously in a series of stirrer vessels.

4. The process of claim 1 wherein the condensation of formaldehyde is carried out continuously in a reaction tube.

5. The process of claim 1 wherein the condensation reaction of formaldehyde takes place in the presence of 0.01 to 10% by weight of catalyst, based on the quantity of reaction mixture.

6. The process of claim 1 wherein the condensation reaction of formaldehyde takes place in the presence of 0.1 to 5% by weight of catalyst, based on the quantity of reaction mixture.

7. The process of claim 1 wherein step (3) comprises lowering the pH of the reaction mixture by from 0.5 to 3.0 units to a pH from 4.0 to 5.7.

8. The process of claim 1 wherein the initial pH is from 6.5 to 7.0, and wherein the pH is then lowered by from 0.8 to 1.7 units to a pH of from 5 to 6.

9. A mixture of hydroxyl compounds prepared according to the process of claim 5.

* * * * *